United States Patent [19]

Reichel

[11] Patent Number: 4,535,178

[45] Date of Patent: Aug. 13, 1985

[54] PROCESS FOR THE PREPARATION OF POLYETHER-ESTER POLYOLS

[75] Inventor: Curtis J. Reichel, Wyandotte, Mich.

[73] Assignee: BASF Wyandotte Corporation, Wyandotte, Mich.

[21] Appl. No.: 426,306

[22] Filed: Sep. 29, 1982

[51] Int. Cl.³ .............................................. C07C 67/08
[52] U.S. Cl. ...................................... 560/91; 560/89; 560/93
[58] Field of Search ............................ 560/91, 89, 93; 252/431 C; 502/171, 325, 340

[56] References Cited

U.S. PATENT DOCUMENTS 3,374,208 3/1968 Seiner et al. .......................... 528/284
3,907,863 9/1975 Voss ...................................... 560/91

Primary Examiner—Natalie Trousof
Assistant Examiner—Vera C. Clarke
Attorney, Agent, or Firm—Norbert M. Lisicki

[57] ABSTRACT

Polyether-ester polyols are prepared by reacting a polyether polyol, tetrahydrophthalic anhydride and an alkylene oxide in the presence of a catalyst selected from the group consisting of calcium naphthenate and cobalt naphthenate. These polyols may be used in preparing polyurethane products.

6 Claims, No Drawings

PROCESS FOR THE PREPARATION OF POLYETHER-ESTER POLYOLS

BACKGROUND OF THE INVENTION

1. Field of the Invention

The present invention relates to a process for the preparation of polyether-ester polyols. More particularly, the invention relates to the preparation of these polyols by reacting a polyether polyol, tetrahydrophthalic anhydride and an alkylene oxide in the presence of an effective amount of a catalyst selected from the group consisting of calcium naphthenate and cobalt naphthenate.

2. Description of the Prior Art

The preparation of polyether-ester polyols by the reaction of an alkylene oxide with a half acid ester obtained by the reaction of a polyol with an unsaturated acid anhydride is well known in the art as taught in U.S. Pat. Nos. 3,931,092, 4,014,846, 4,093,573 and 4,144,395. These patents relate to uncatalyzed or trialkylamine-catalyzed reactions. U.S. Pat. No. 3,374,208 teaches the use of various metal catalysts for the preparation of polyesters. The prior art, however, does not teach the preparation of polyether-ester polyols having an acidity of less than 1 mg KOH/gm of sample employing the process of the instant invention.

SUMMARY OF THE INVENTION

This invention is directed to an improvement in the process for preparing polyether-ester polyols comprising reacting a polyether polyol, tetrahydrophthalic anhydride, and an alkylene oxide in the presence of an effective amount of a catalyst selected from the group consisting of calcium naphthenate and cobalt naphthenate.

DESCRIPTION OF THE PREFERRED EMBODIMENTS

In the preferred embodiment for the preparation of these polyether-ester polyol a polyoxyalkylene polyether polyol is reacted with tetrahydrophthalic anhydride to form a half acid ester in the presence of an effective amount of a catalyst selected from the group consisting of calcium naphthenate and cobalt naphthenate followed by a reaction with an alkylene oxide at temperatures from about 75° C. to about 175° C., preferably at about 125° C. to produce a polyether-ester polyol having an acid number of less than about 5 mg KOH/gram of sample. The concentration of catalyst which may be employed ranges from 0.005 to 0.5 weight percent based on the weight of polyol mixture.

The organic compounds may be glycerine, trimethylolpropane, trimethylolethane, 1,2,6-trihydroxyhexane and the like.

The alkylene oxides which may be employed for the preparation of the polyetherester polyols include ethylene oxide, propylene oxide, butylene oxide, amylene oxide and mixtures of these oxides.

Representative polyols which may be employed in the subject invention are well known to those skilled in the art. They are often prepared by the catalytic condensation of an alkylene oxide or mixture of alkylene oxides either simultaneously or sequentially with an organic compound having at least two active hydrogen atoms, such as evidenced by U.S. Pat. Nos. 1,922,459; 3,190,927; and 3,346,557. Representative polyols include polyhydroxyl-containing polyesters, polyoxyalkylene polyether polyols, polyhydroxy-terminated polyurethane polymers, polyhydroxyl-containing phosphorus compounds, and alkylene oxide adducts of polyhydric polythioesters, polyacetals, aliphatic polyols and thiols, ammonia, and amines including aromatic, aliphatic, and heterocyclic amines, as well as mixtures thereof. Alkylene oxide adducts of compounds which contain 2 or more different groups within the above-defined classes may also be used, for example, amino alcohols which contain an amino group and a hydroxyl group. Also, alkylene oxide adducts of compounds which contain one SH group and one OH group as well as those which contain an amino group and an SH group may be used. Generally, equivalent weight of the polyols will vary from 100 to 10,000, preferably from 1000 to 3000.

Any suitable polyoxyalkylene polyether polyol may be used such as the polymerization product of an alkylene oxide or a mixture of alkylene oxides with a polyhydric alcohol. Any suitable polyhydric alcohol may be used such as those disclosed above for use in the preparation of the hydroxy-terminated polyesters. Any suitable alkylene oxide may be used such as ethylene oxide, propylene oxide, butylene oxide, amylene oxide, and mixtures of these oxides. The polyoxyalkylene polyether polyols may be prepared from other starting materials such as tetrahydrofuran and alkylene oxide-tetrahydrofuran mixtures; epihalohydrins such as epichlorohydrin; as well as aralkylene oxides such as styrene oxide. The polyoxyalkylene polyether polyols may have either primary or secondary hydroxyl groups. Included among the polyether polyols are polyoxyethylene glycol, polyoxypropylene glycol, polyoxybutylene glycol, polytetramethylene glycol, block copolymers, for example, combinations of polyoxypropylene and polyoxyethylene glycols, poly-1,2-oxybutylene and polyoxyethylene glycols, poly-1,4-oxybutylene and polyoxyethylene glycols, and random copolymer glycols prepared from blends of two or more alkylene oxides or by the sequential addition of two or more alkylene oxides. The polyoxyalkylene polyether polyols may be prepared by any known process such as, for example, the process disclosed by Wurtz in 1859 and *Encyclopedia of Chemical Technology*, Vol. 7, pp. 257-262, published by Interscience Publishers, Inc. (1951) or in U.S. Pat. No. 1,922,459. Polyethers which are preferred include the alkylene oxide addition products of trimethylolpropane, glycerine, pentaerythritol, sucrose, sorbitol, propylene glycol, and 2,2'-(4,4'-hydroxyphenyl)propane and blends thereof having equivalent weights of from 100 to 5000.

Suitable polyhydric polythioethers which may be condensed with alkylene oxides include the condensation product of thiodiglycol or the reaction product of a dicarboxylic acid such as is disclosed above for the preparation of the hydroxyl-containing polyesters with any other suitable thioether glycol.

Polyhydroxyl-containing phosphorus compounds which may be used include those compounds disclosed in U.S. Pat. No. 3,639,542. Preferred polyhydroxyl-containing phosphorus compounds are prepared from alkylene oxides and acids of phosphorus having a $P_2O_5$ equivalency of from about 72 percent to about 95 percent.

Suitable polyacetals which may be condensed with alkylene oxides include the reaction product of formaldehyde or other suitable aldehyde with a dihydric alcohol or an alkylene oxide such as those disclosed above.

Suitable aliphatic thiols which may be condensed with alkylene oxides include alkanethiols containing at least two —SH groups such as 1,2-ethanedithiol, 1,2-propanedithiol, 1,3-propanedithiol, and 1,6-hexanedithiol; alkene thiols such as 2-butene-1,4-dithiol; and alkyne thiols such as 3-hexyne-1,6-dithiol.

Suitable amines which may be condensed with alkylene oxides include aromatic amines such as aniline, o-chloroaniline, p-aminoaniline, 1,5-diaminonaphthalene, methylene dianiline, the condensation products of aniline and formaldehyde, and 2,3- 2,6-, 3,4-, 2,5-, and 2,4-diaminotoluene; aliphatic amines such as methylamine, triisopropanolamine, ethylenediamine, 1,3-diaminopropane, 1,3-diaminobutane, and 1,4-diaminobutane.

Also, polyols containing ester groups can be employed in the subject invention. These polyols are prepared by the reaction of an alkylene oxide with an organic dicarboxylic acid anhydride and a compound containing reactive hydrogen atoms. A more comprehensive discussion of these polyols and their method of preparation can be found in U.S. Pat. Nos. 3,585,185; 3,639,541 and 3,639,542.

The unsaturated polyols of the instant invention may be prepared by the reaction of any conventional polyol such as those described above with tetrahydrophthalic anhydride. The amount of unsaturation may range from about 0.05 to about 3.0 moles of unsaturation per mole of polyol, preferably from 0.3 to 1.0 moles of unsaturation per mole of polyol.

In addition to being useful in the preparation of polyurethanes, the polyols prepared in accordance with the process of the subject invention find utility as precursors in the preparation of graft polymer dispersions as disclosed in U.S. Pat. Nos. 3,652,658, 3,875,258, 3,950,317 and 3,953,393.

The following examples illustrate the nature of the invention. All parts are by weight unless otherwise indicated.

The following abbreviations are employed in the examples below:

Polyol A is a trimethylolpropane, propylene oxide, ethylene oxide heteric adduct containing 15 percent ethylene oxide and having a hydroxyl number of 25.

Polyol B is a glycerine, propylene oxide, ethylene oxide adduct containing a 15 percent ethylene oxide cap and having a hydroxyl number of 25.

Catalyst A is calcium naphthenate.

Catalyst B is cobalt naphthenate.

PROCEDURE

Into a 5 liter round bottom flask, 2000 grams of the polyol as designated in the Table, 59.1 grams of tetrahydrophthalic anhydride and the catalyst at the designated concentrations were charged. The contents were heated at 125° C. for 3 hours. The reaction product was transferred to a 1 gallon steam heated stainless steel autoclave, heated to 125° C., pressurized with nitrogen and 96 grams of ethylene oxide were added. The resulting mixture was then reacted for 8 hours at 125° C. The product was discharged from the autoclave and stripped of volatiles by heating at 125° C. for 1 hour at <10 mm Hg pressure. The resulting products had the physical properties as tabulated in the Table.

TABLE

| Examples | THDA Equivalents* | Catalyst | Catalyst Level, ppm | OH No. | Acid No. | Saponification No. | Unsaturation | Viscosity cps, 25° C. | Polyol |
|---|---|---|---|---|---|---|---|---|---|
| 1 | 1.0 | A | 800 | 26.8 | 0 | 20.9 | 0.6 | 6470 | A |
| 2 | 1.0 | A | 400 | 23.4 | 2.1 | 21.5 | 0.13 | 2300 | A |
| 3 | 1.0 | A | 200 | 19.8 | 5.41 | 21.6 | 0.15 | 1852 | A |
| 4 | 1.0 | B | 1000 | — | — | — | — | — | A |
| 5 | 1.5 | B | 1000 | 24.5 | 0 | 31.3 | 0.23 | 1680 | A |
| 6 | 1.0 | B | 1000 | 24.4 | 0 | 21.4 | 0.18 | 2285 | A |
| 7 | 0.8 | — | — | 11.3 | 7.0 | 17.2 | 0.19 | 1815 | A |
| 8 | 0.8 | — | — | 14.8 | 5.2 | 17.2 | 0.20 | 1905 | B |

*Tetrahydrophthalic anhydride equivalents per mole of polyol.

The embodiments of the invention in which an exclusive privilege or property is claimed are defined as follows:

1. In a process for the preparation of polyether-ester polyols by the reaction of a polyether polyol and tetrahydrophthalic anhydride to form a half acid ester followed by the reaction of the half acid ester with an alkylene oxide to obtain a product having an acid number of less than about 5 mg KOH/gm the improvement which comprises conducting the reaction between the polyether polyol and the anhydride and the following reaction with the alkylene oxide in the presence of an effective amount of a catalyst selected from the group consisting of calcium naphthenate and cobalt naphthenate.

2. The process of claim 1 wherein the concentration of the catalyst employed is from 0.005 to 0.5 weight percent based on the weight of polyol.

3. The process of claim 1 wherein the polyether polyol is the reaction product of a polyhydric alcohol and an alkylene oxide selected from the group consisting of ethylene oxide, propylene oxide and butylene oxide.

4. The process of claim 1 wherein the alkylene oxide is ethylene oxide.

5. The process of claim 1 wherein the alkylene oxide is propylene oxide.

6. The process of claim 1 wherein the reaction temperature is from about 75° C. to about 175° C.

* * * * *